US007331342B2

(12) United States Patent
Spearman et al.

(10) Patent No.: US 7,331,342 B2
(45) Date of Patent: Feb. 19, 2008

(54) OXYGEN HUMIDIFIER

(76) Inventors: Michael Spearman, 2 Lacewing Pl., The Woodlands, TX (US) 77380; John H. Burban, 9612 57th St. North, Lake Elmo, MN (US) 55042; Robert O. Crowder, 6345 W. Shadow Lake Dr., Lino Lakes, MN (US) 55014; Carl M. Geisz, 1150 Cushing Cir., Apt. 146, St. Paul, MN (US) 55108

( * ) Notice: Subject to any disclaimer, the term of this patent is extended or adjusted under 35 U.S.C. 154(b) by 161 days.

(21) Appl. No.: 10/958,973

(22) Filed: Oct. 5, 2004

(65) Prior Publication Data

US 2005/0072425 A1   Apr. 7, 2005

Related U.S. Application Data

(60) Provisional application No. 60/509,115, filed on Oct. 6, 2003.

(51) Int. Cl.
  *A61M 15/00* (2006.01)
  *A62B 18/00* (2006.01)
(52) U.S. Cl. .................. 128/203.14; 128/200.24; 128/203.16; 128/203.17
(58) Field of Classification Search .......... 128/203.16, 128/203.12, 203.17, 203.25, 203.26, 201.13, 128/204.17, 200.24, 205.27, 205.29, 206.16, 128/205.12, 203.27, 203.14
See application file for complete search history.

(56) References Cited

U.S. PATENT DOCUMENTS 4,326,513 A * 4/1982 Schulz et al. .......... 128/203.14
4,449,992 A * 5/1984 Yamada et al. .............. 96/7
4,681,099 A * 7/1987 Sato et al. ............ 128/204.23
6,248,153 B1 * 6/2001 Braun et al. ............... 95/45
6,361,588 B1 * 3/2002 Moratalla ..................... 96/4
6,511,526 B2   1/2003 Jagger et al. ............... 95/96
6,551,384 B1   4/2003 Ackley et al. .............. 95/96
6,558,451 B2   5/2003 McCombs et al. ......... 95/98
6,629,525 B2  10/2003 Hill et al. .............. 128/202.26

OTHER PUBLICATIONS

N. Burioka et al. "Membrane Humidifier That Does Not Require Addition of Water." Yonago Acta Medica. Aug. 1999.*
Naoto Burioka, Kazukiyo Takano, Eiji Hashino, Hisashi Suyama, Shinji Saito, and Takao Sasaki; Clinical Utility of a Newly Developed Pressure Swing Adsorption-Type Oxygen Concentrator With a Membrane Humdifier; *Respiration*, 1997; 64: pp. 268-272.

(Continued)

*Primary Examiner*—Justine R. Yu
*Assistant Examiner*—Shumaya B. Ali
(74) *Attorney, Agent, or Firm*—Jacobson and Johnson

(57) ABSTRACT

An apparatus and method for separating breathable oxygen gas from a source of gas and then humidifying the oxygen gas while preventing over humidification of the oxygen gas, the apparatus comprising a gas pathway located on a first side of a water transfer member, an oxygen gas pathway located on a second side of the water transfer member and a separator for separating the breathable oxygen gas from a gas located on the first side of the water transfer member and directing the breathable oxygen gas past the second side of the water transfer member while maintaining the pressure of the gas substantially equal to the pressure of the breathable oxygen gas to thereby humidify the breathable oxygen gas while preventing a moisture condensation in the breathable oxygen gas.

13 Claims, 6 Drawing Sheets

OTHER PUBLICATIONS

Naoto Burioka, Hiroki Chikumi, Hisahi Suyama, Takanori Sako, Hidemi Teramoto; Yukio Matsumoto, and Kazukiyo Takano; Membrane Humidifier That Does Not Require Addition of Water; *Yonago Acta medica*, 1999; 42: pp. 185-188.

Naoto Burioka, Kazukiyo Takano, Hiroki Chikumi, Eiji Hashino, and Takao Sasaki; Efficacy of Newly Developed Pressure Swing Adsorption Type Oxygen Concentrator With Membrane Humidifier Comparision With Conventional Oxygen Concentrator With Bubble Humidifier; *Internal Medicine*; Dec. 1997; vol. 36, No. 12.

Naoto Burioka et al., Yonago Acta Medica: *Membrane Humidifier That Does Not Require Additional of Water*, 1999, pp. 185-188.

\* cited by examiner

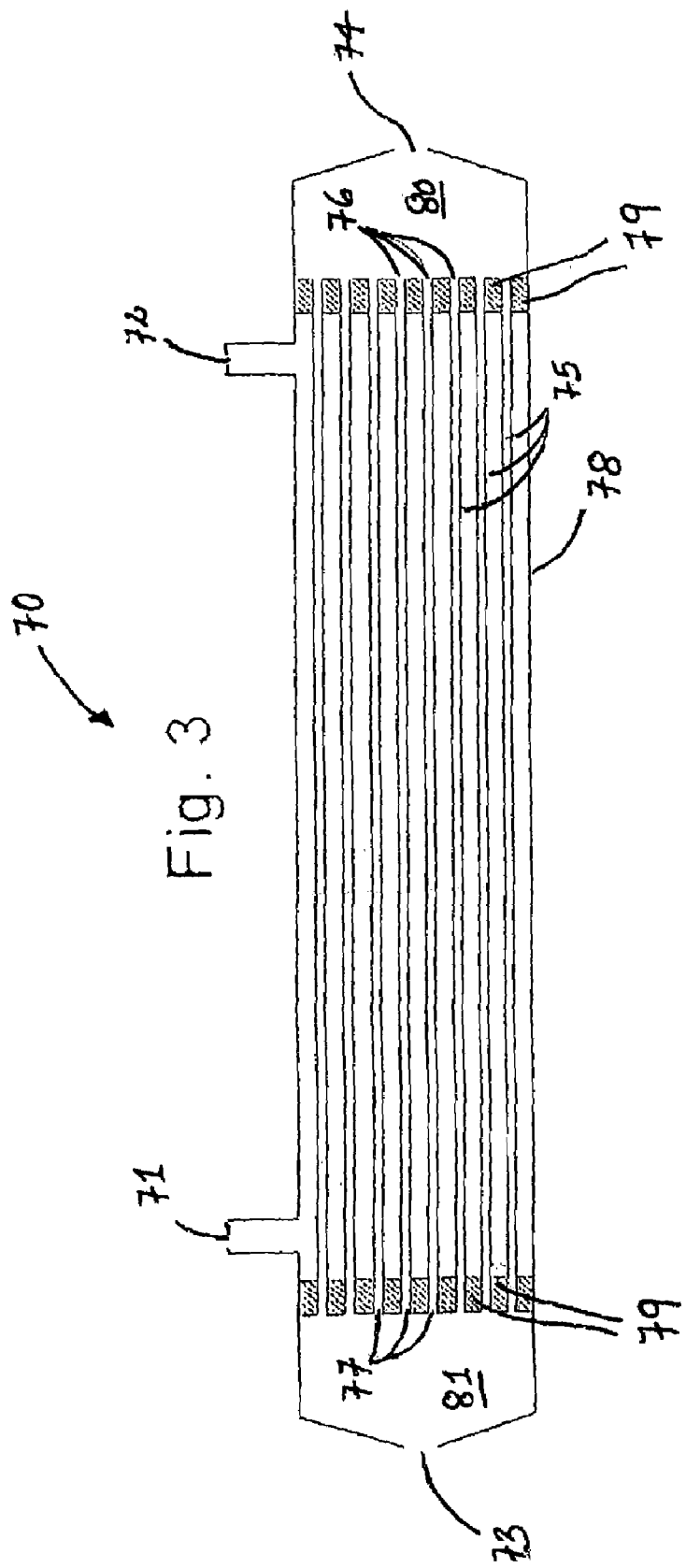

OXYGEN HUMIDIFIER

CROSS REFERENCE TO RELATED APPLICATIONS

This application claims priority to pending U.S. Provisional Application Ser. No. 60/509,115, which was filed on Oct. 6, 2003.

FIELD OF THE INVENTION

The present invention relates to humidification of a breathable oxygen and more specifically, to humidifying of breathable oxygen such as an oxygen-enriched gas while minimizing the possibility of condensation and bacterial growth.

STATEMENT REGARDING FEDERALLY SPONSORED RESEARCH OR DEVELOPMENT

None

REFERENCE TO A MICROFICHE APPENDIX

None

BACKGROUND OF THE INVENTION

Oxygen concentrators to produce breathable oxygen for a person requiring an oxygen-enriched atmosphere generally operate in the following manner. A compressor supplies compressed ambient air to a bed of molecular sieves. The molecular sieves adsorb nitrogen gas from the compressed ambient air to provide a gas with a high oxygen content. The oxygen-enriched gas then exits the bed of molecular sieves and passes through a regulator and a patient adjustable needle valve, which controls the gas flow rate. The oxygen-enriched gas can then be supplied to a patient who can breath the oxygen-enriched gas. In general, most oxygen concentrators contain two beds of molecular sieves. While one bed of molecular sieves is in operation to produce the oxygen-enriched gas, the second bed of molecular sieves is being purged of the adsorbed nitrogen in order to regenerate the bed of molecular sieves. The two beds of molecular sieves allow the oxygen concentrator to supply a continuous flow of an oxygen-enriched gas to the patient. Oxygen concentrators manufactured by Invacare®, Respironics®, and Sunrise® use two beds of molecular sieves for the creation of a continuous supply of an oxygen-enriched gas from a source of ambient air.

One of the problems that arises in the use of the molecular sieves is that the molecular sieves not only adsorb nitrogen, but also water vapor. Thus the oxygen-enriched gas being delivered to the patient can be extremely dry, typically with a dew point of –40° F. or lower (a relative humidity of less than 0.5%). The dry gas can cause dehydration of the nasal passages and respiratory system, which can lead to patient discomfort and irritation.

There are existing humidifiers for humidifying oxygen-enriched gas flowing to the patient. These humidifiers generally have a source of liquid water positioned to allow the oxygen-enriched gas to bubble through the liquid water, thus humidifying the oxygen-enriched gas. While these humidifiers work for humidifying the oxygen flow, they do have several major drawbacks. First, unless the water is re-supplied, eventually the water completely evaporates, ending all humidification. Second, standing water offers a site for bacterial growth. This is especially true since the water for the bubbler is usually, located on the exterior of the oxygen concentrator, and thus is open to environmental contamination.

In addition, bacteria growing in standing water can become aerosolized during the bubbling process and be carried along with the oxygen-enriched gas, potentially reaching to the patient. Third, manufacturers of oxygen concentrators often go to great lengths to minimize the noise output of their oxygen concentrators. Providing for a source of liquid water for humidifying oxygen-enriched gas located outside a cabinet of the oxygen concentrators and thus outside of the oxygen concentrators' noise abatement measures can contribute significantly to the noise generated by the oxygen concentrator through the noisy bubbling action.

The use of membrane devices to humidify oxygen-enriched gas is also known in the art. These membrane devices work by using selective membranes to transfer moisture from one gas to another gas without significant transfer of other components. This transfer of moisture from one gas to another gas is accomplished by using a membrane having a greater selectivity for water over the other components such as both oxygen and nitrogen. The selectivity of a membrane for water compared to oxygen and nitrogen is defined by the ratio of the water permeability to the permeability of either the oxygen or nitrogen. It is noted that the aforementioned selective membranes have a selectivity for water over oxygen or nitrogen of greater than 1, more preferably greater than 10, and most preferably greater than 100.

In use, the above-mentioned membrane device is in contact with both a high-pressure compressed stream of gas exiting the compressor and a lower-pressure oxygen-enriched stream of gas exiting a regulator and needle valve. Moisture passes from the high-pressure compressed stream of gas through the selective membrane to the lower-pressure oxygen-enriched stream of gas.

The use of membrane devices for gas humidification have advantages over oxygen concentrators that humidify their gases with bubblers. Firstly, the operator never needs to fill or refill the membrane devices with water as moisture for humidification is obtained from ambient air. Secondly, oxygen concentrators that humidify through the use of membrane devices are quieter than oxygen concentrators that humidify with bubblers as the membrane devices do not contribute to the sound produced by the oxygen concentrators.

Membrane devices such as the ones disclosed in the articles of *Yonago Acta Medica,* 1999; 42: 185-188 and *Internal Medicine,* Vol. 36, No. 12 (December 1997) do have one major problem in that membrane devices introduce the possibility of over humidifying the oxygen-enriched gas. This over humidification introduces the possibility of condensation and thus bacterial growth. More specifically, since membrane devices used in oxygen concentrators are usually installed down stream of the compressor, the partial pressure of the water vapor is frequently above the vapor pressure of water at room temperature. It is noted that since the stream of gas coming out of the compressor is usually at a temperature that is greater than the ambient temperature there is not necessarily condensation inside the membrane device. However, the lower-pressure stream of oxygen-enriched gas that enters the membrane device from the regulator and needle valve can become humidified to a partial pressure that is likely above the room temperature vapor pressure. This means that as the oxygen-enriched gas cools enroot to the patient, condensation can occur. This not only means that the patient can periodically receive liquid water, but also that there exists a risk of bacterial growth.

There are two current methods for dealing with the issue of over humidification by the membrane devices. Firstly, the membrane devices can be used in an environment where the ambient humidity never exceeds an amount that would cause the oxygen-enriched gas to become over humidified. However, since many of these devices are used in patient's home under a variety of environmental conditions, the ambient humidity is difficult to control. Secondly, a shunt can be installed so that a portion of the oxygen-enriched gas bypasses the membrane device, remaining at an extremely low humidity. When the streams of oxygen-enriched gas are later remixed, an optimal humidity can be achieved. This system however, requires adjustment by the user to match ambient conditions as well as requiring additional valves and tubing.

SUMMARY OF THE INVENTION

An apparatus and method for humidifying an oxygen-enriched gas while preventing over humidification of the oxygen-enriched gas. The apparatus comprising a gas pathway on a first side of a water transfer member such as a membrane device having a selective membrane with a greater selectivity for water over both nitrogen and oxygen, an oxygen-enriched gas pathway located on a second side of the water transfer member and a separator for separating a breathable oxygen from a gas located in the first side of the water transfer member and directing the breathable oxygen past the second side of the water transfer member while maintaining the pressure of the gas in the first side of the water transfer member substantially equal to the pressure of the breathable oxygen-enriched gas in the second side of the water transfer member to thereby humidify the breathable oxygen while preventing moisture condensation in the breathable oxygen.

In one embodiment of the present invention the membrane device is installed in the oxygen concentrator such that the membrane device engages a stream of ambient air prior to the compression of the ambient air by a compressor while an oxygen-enriched gas engages the membrane device after the oxygen-enriched gas has engaged a regulator and needle valve. In an alternative embodiment of the present invention, the membrane device is installed in an oxygen concentrator such that the membrane device engages the stream of ambient air after compression of the ambient air by the compressor while the oxygen-enriched gas engages the membrane device prior to the engagement of the oxygen-enriched gas with the gas regulator.

BRIEF DESCRIPTION OF THE DRAWINGS

FIG. 3 is a cross sectional view of a hollow fiber membrane device that could be used in an oxygen concentrator for humidification;

DESCRIPTION OF THE PREFERRED EMBODIMENT

Figure 1:
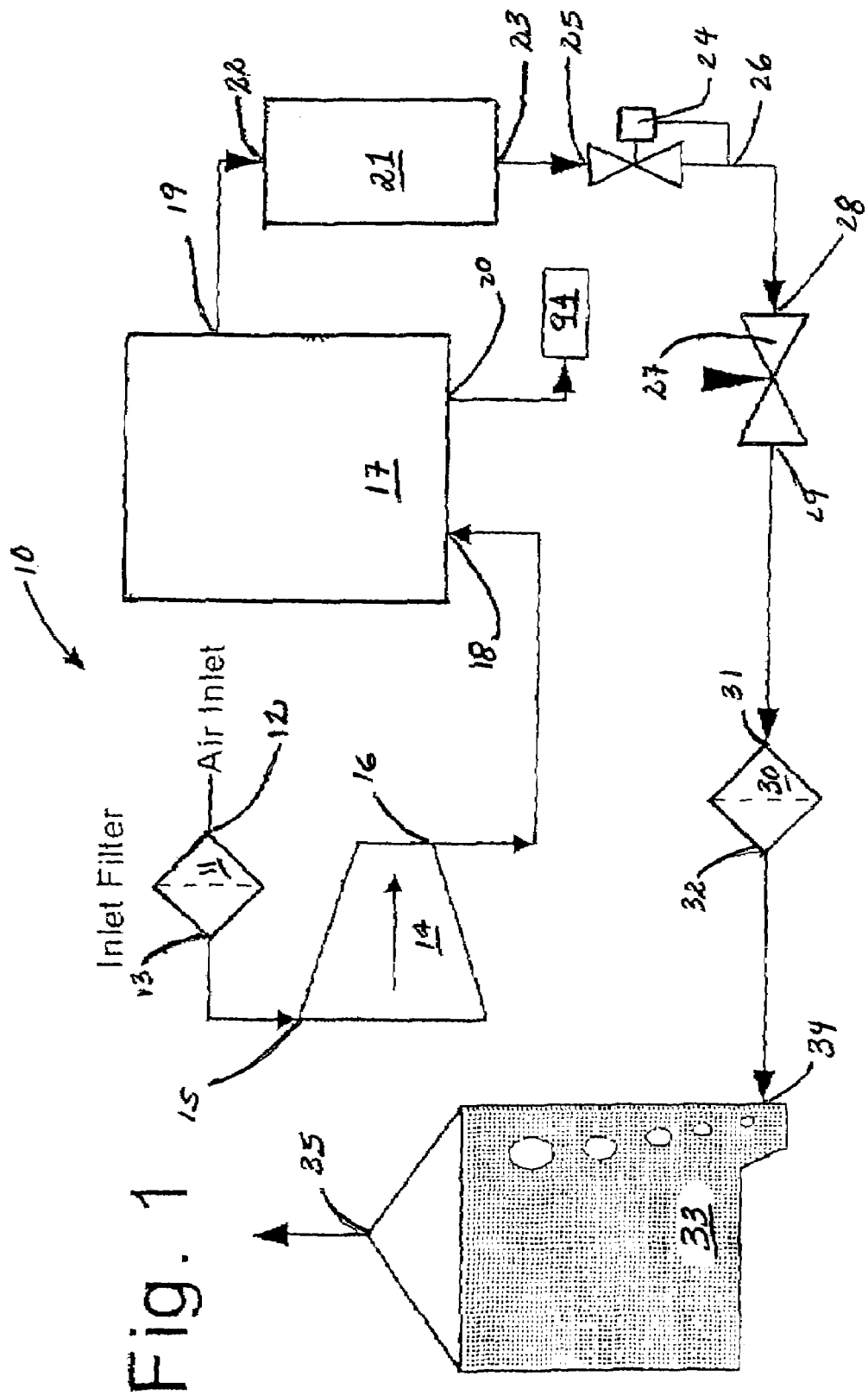
FIG. 1 is a diagrammatic view of a prior art oxygen concentrator using a bubbler for humidification of the oxygen-enriched gas.

Referring to FIG. 1, FIG. 1 shows a typical oxygen concentrator 10 which uses a bubbler 33 for humidification. In the oxygen concentrator 10 of FIG. 1, ambient air is drawn into an inlet 12 of an inlet filter 11. The inlet filter 11 functions to remove a portion of the particulates and bacteria from the ambient air. Inlet filter 11 includes an outlet 13 that is in fluid communication with an inlet 15 of a compressor 14 for increasing the pressure of the ambient air. An outlet 16 of the compressor 14 is in fluid communication with an inlet 18 of an adsorption bed 17, adsorption bed 17 comprising of molecular sieves for enriching the gas with oxygen by removing nitrogen therefrom.

In regards to adsorption bed 17, adsorption bed 17 actually is comprised of more than one (1) bed of sieves, as described earlier, and includes a switching valve and associated controls. For simplicity, we describe adsorption bed 17 as a single unit.

The adsorption bed 17 includes an outlet 19 and an outlet 20. A portion of the gas that flows through the adsorption bed 17 that is enriched in oxygen and depleted of moisture discharges through outlet 19 at a pressure close to the pressure of the entering air at inlet 18. Another portion of the gas enriched in nitrogen and moisture discharges through outlet 20 during the regeneration stage. As shown in FIG. 1, outlet 20 is in fluid communication with a muffler 94, which quiets the oxygen-depleted air as it exits the system.

A buffer tank 21 having an inlet 22 in fluid communication with the outlet 19 of the adsorption bed 17 and an outlet 23 in fluid communication with an inlet 25 of a pressure regulator 24 function to smooth out fluctuations in pressure and flow of the oxygen-enriched gas from the adsorption bed 17.

The pressure regulator 24 having outlet 26 in fluid communication with an inlet 28 of flow control valve 27 maintains a constant pressure of oxygen-enriched gas flowing to the flow control valve 27 while the flow control valve 27 maintains a constant flow rate. The combination of the pressure regulator 24 and the flow control valve 27 provides a constant flow of oxygen-enriched gas to the patient.

Oxygen concentrator 10 also includes an outlet filter 30 having an inlet 31 and an outlet 32, inlet 31 being in fluid communication with the outlet 29 of the valve 27. Outlet filter 30 functions as a final safety device by preventing unwanted materials from reaching the patient while simultaneously preventing foreign materials and bacteria from entering into the oxygen concentrator 10 when it is not in use.

Oxygen concentrator 10 further includes a bubbler 33 generally located external of oxygen concentrator 10 for humidification of the oxygen-enriched gas. In the aforementioned arrangement, any humidification of the oxygen-enriched gas takes place outside the oxygen concentrator 10 at the bubbler 33. Bubbler 33 includes an inlet 34 and an outlet 35 with the inlet 34 being in fluid communication with the outlet 32 of the outlet filter 30.

Figure 2:
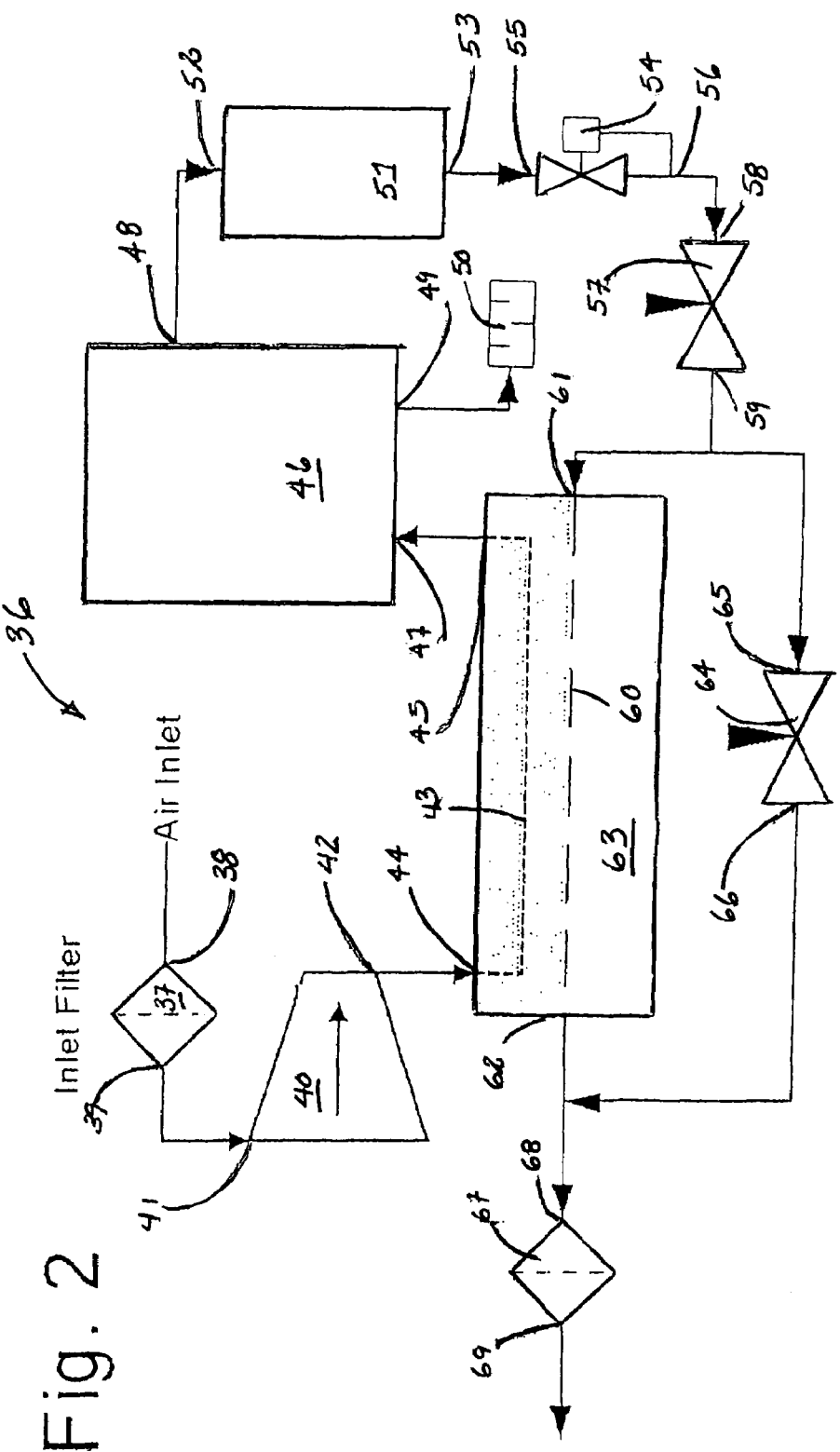
FIG. 2 is a diagrammatic view of a prior art oxygen concentrator using a membrane device for humidification of the oxygen-enriched gas.

Referring to FIG. 2, FIG. 2 is another embodiment of a prior art oxygen concentrator 36 that uses a membrane device 63 to humidify the oxygen-enriched gas.

As shown in FIG. 2, ambient air is drawn into an inlet 38 of an inlet filter 37. In regards to inlet filter 37, inlet filter 37 functions to allow ambient air into oxygen concentrator 36 while simultaneously blocking particulates and bacteria from entering into oxygen concentrator 36. Inlet filter 37 includes an outlet 39 in fluid communication with an inlet 41 of a compressor 40.

Referring to FIG. 2, the membrane device 63 of oxygen concentrator 36 comprises a membrane (shown for example in FIG. 3A) having a greater selectivity for water over both oxygen and nitrogen. Membrane device 63 includes a first pathway 43 and a second pathway 60, the two pathways separated by a selective membrane. The first pathway 43 includes an inlet 44 and an outlet 45 and the second fluid pathway 60 includes an inlet 61 and an outlet 62. Fluid pathway 43 is shown in FIG. 2 designated by a dotted line and fluid pathway 60 is shown designated by a dashed line wherein an outlet 42 of compressor 40 is in fluid communication with the inlet 44 of the membrane device 63 and an inlet of 47 of an adsorption bed 46 is in fluid communication with the outlet 45 of the first pathway 43.

The adsorption bed 46 includes an outlet 48 and an outlet 49. A portion of the gas flowing through the adsorption bed 46 is enriched in oxygen and depleted of moisture is discharged through outlet 48 at a pressure close to the pressure of the entering air at inlet 47. Another portion of the gas enriched in nitrogen and moisture discharges through outlet 49 during the regeneration stage. Outlet 49 is shown in FIG. 2 fluid communication with a muffler 50, muffler 50 providing sound abatement by quieting the oxygen-depleted air as it exits the system.

A buffer tank 51 having an inlet 52 in fluid communication with the outlet 48 of the adsorption bed 46 and an outlet 53 in fluid communication with an inlet 55 of the pressure regulator 54 smoothes out fluctuations in pressure and flow of oxygen-enriched gas from the adsorption bed.

Referring to FIG. 2, pressure regulator 54 having an outlet 56 in fluid communication with an inlet 58 of a flow control valve 57 maintains a constant pressure of oxygen-enriched gas flow to a flow control valve 57. The flow control valve 57 having an outlet 59 in fluid communication with the inlet 61 of the membrane device 63 maintains a constant flow rate of oxygen-enriched gas. The combination of the pressure regulator 54 and the flow control valve 57 provides a constant flow of oxygen-enriched gas to the patient.

In regards to membrane device 63, while the selective membrane in membrane device 63 permits water vapor to pass from fluid pathway 43 to fluid pathway 60, other gases such as oxygen and nitrogen are hindered from passing therethrough. Since the oxygen-enriched gas entering membrane device 63 at inlet 61 is extremely dry, there exists a driving force for water vapor to pass across the selective membrane from the high-pressure compressed air in pathway 43 to the lower pressure dry oxygen-enriched gas located in pathway 60. Thus the humidity of the oxygen-enriched gas is higher when the oxygen-enriched gas exits the membrane device 63 at outlet 62 than when the oxygen-enriched gas enters membrane device 63 at inlet 61. It is noted that while the membrane selectivity is high, the oxygen level is changed only by dilution with water vapor.

It is noted that those skilled in the art will realize that the diffusion of water vapor across the selective membrane is driven by a difference in chemical potential of water in the two gases. Those skilled in the art will also realize the chemical potential difference can be substituted with a concentration difference or partial pressure difference in this case by a change in the mass transfer coefficient which relates driving force with flux across the membrane. This means that once the partial pressure of water in the lower pressure oxygen-enriched gas in the membrane device 63 approaches the partial pressure of the stream of higher pressure air in pathway 43, the driving force for water transfer drops to zero, and thus the water flux drops to zero. This mean that the partial pressure of water in the oxygen-enriched gas exiting the membrane device 63 at outlet 62 can not be higher than the partial pressure of water in the stream of air entering membrane device 63 at inlet 44.

To draw a parallel to a heat exchanger, the stream being heated can never leave the heat exchanger hotter than the heating stream enters the heat exchanger. If the membrane device 63 is functioning well, the partial pressure of water in the oxygen-enriched stream leaving at outlet 62 will be close to the partial pressure of water in the air stream entering at inlet 44. This is especially true since the airflow from first inlet 44 to the first outlet 45 of membrane device 63 is usually significantly greater than the oxygen-enriched gas flowing from the second inlet 61 to the outlet 62 of pathway 60.

Since the partial pressure of water in the stream of air entering membrane device 63 at inlet 44 is increased from the ambient partial pressure of water by the compression ratio, it can be significantly higher than the vapor pressure of water at ambient temperature. Since the temperature of the air entering at inlet 44 is also increased from ambient temperature by compression, and this heat is transferred to the oxygen-enriched gas in the membrane device 63 by the movement of the heated moisture, there will most likely not be condensation anywhere in membrane device 63. However, if the oxygen-enriched air stream exiting membrane device 63 were allowed to cool to ambient temperature to enable a patient to breath the oxygen-enriched air, harmful condensation can occur.

In order to alleviate the condensation problem the prior art oxygen concentrator of FIG. 2, includes a bypass valve 64, the bypass valve 64 having an inlet 65 and an outlet 66, the outlet 66 is in fluid communication with the outlet 62 of membrane device 63 and an inlet 68 of the outlet filter 67, which does any final filtration and system protection before the oxygen-enriched gas is delivered to the patient via an outlet 69 of outlet filter 67. Bypass valve 64 is adjusted such that a portion of the oxygen-enriched gas bypasses the membrane device 63 and thus remains extremely dry. If bypass valve 64 is adjusted correctly, the oxygen-enriched gas from the second outlet 62 of membrane device 63 and from the outlet 66 of bypass valve inlet 64 combine and produce a mixed partial pressure of water that is below the vapor pressure of water at ambient temperature, thereby preventing condensation down stream as the oxygen-enriched gas cools to ambient temperature. However, if bypass valve 64 is adjusted incorrectly than either too much or too little oxygen-enriched gas will bypass the membrane device 63 thus resulting in either condensation in the oxygen-enriched gas downstream or insufficient humidification of the oxygen-enriched gas. Since the adjustment of bypass valve 64 must match current ambient conditions, bypass valve 64 is required to be adjusted by the patient as environmental conditions such as ambient temperature, ambient humidity, and total oxygen-enriched gas flow changes.

Referring to FIG. 3, FIG. 3 shows an embodiment of a membrane device 70 used in the oxygen concentrator of the present invention that eliminated the need to mix the flows as shown in FIG. 2. Although the membrane device 70 shown in FIG. 3 comprises a hollow fiber membrane device, a flat sheet membrane or a spiral wound membrane device could also be used to accomplish the same task. Membrane device 70 includes a first air inlet 71, a first air outlet 72, a second gas inlet 74 and a second gas outlet 73.

In a hollow fiber membrane device 70 as shown in FIG. 3, the membrane comprises the shape of a plurality of tubes with each of the tubes being called a hollow fiber and is represented by reference numeral 75. The materials of the plurality of hollow fiber 75 are chosen such that water vapor can permeate across the hollow fiber 75 more easily than either oxygen or nitrogen. As shown in FIG. 3, each of the plurality of hollow fiber 75 comprises a hollow fiber inlet 76 and a hollow fiber outlet 77 that are in fluid communication with each other down the interior of the hollow fiber 75. The hollow fibers 75 are placed into a shell 78 to make up the module. The bundle of hollow fibers 75 are sealed by a potting compound 79 at both ends so that the interiors of the hollow fibers 75 are not in fluid communication with the exterior of the hollow fibers 75.

As further shown in FIG. 3, the second inlet 74 of the membrane device 70 is in fluid communication with an inlet plenum 80. The inlet plenum 80 is also in fluid communication with the inlet 76 of the hollow fibers 75. The second outlet 73 of the membrane device 70 is in fluid communication with an outlet plenum 81. The outlet plenum 81 is also in fluid communication with the outlet 77 of the hollow fibers 75. The first inlet 71 of the membrane device 70 is in fluid communication with the first outlet 72 of the membrane device 70 along the exterior of the hollow fibers 75.

Although the hollow fiber module is shown in FIG. 3 operating with the air located on the inside of the hollow fibers 75 and the oxygen-enriched gas located on the outside of the hollow fibers 75 flowing counter-currently, the present module would also work using cross or co-current flow, or with the air on the outside of the hollow fibers 75 and the oxygen-enriched gas on the inside of the hollow fibers 75.

Figure 3A:
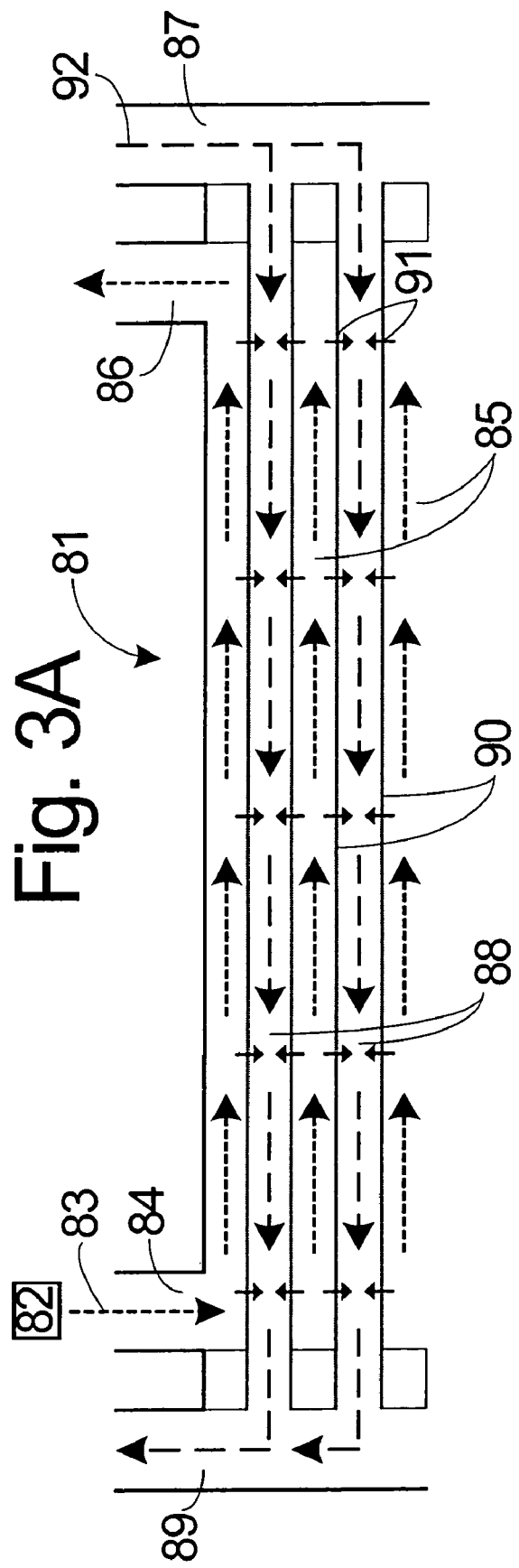
FIG. 3A is a cross sectional view showing the transfer of moisture from a first stream of gas to a second gas located in the membrane device.

Referring to FIG. 3A, FIG. 3A is a cross-sectional view showing the operation of a membrane device 81. In the operation of membrane device 81 a stream of ambient air represented by reference number 83, is directed from an inlet filter 82 into a first inlet 84 of the membrane device 81. Once in membrane device 81 the stream of ambient air 83 is directed through a first pathway 85 of membrane device 81. Once ambient air 83 reaches the end of membrane device 81, the ambient air 83 is then directed out of membrane device 81 through a first outlet 86 of membrane device 81 for separation to an oxygen-enriched stream.

As previously noted, the process of oxygenating the stream of air 83 results in a depletion of moisture from the air 83, which can cause patient discomfort when the dry oxygenated air stream is fed to a patient. In order to solve the aforementioned problem, the now oxygen-enriched but dry air 92, shown as dotted lines, is redirected back into membrane device 81 by way of a second inlet 87 through a second pathway 88 of the membrane device 81 for humidification.

As shown in FIG. 3A, a selective membrane 90 located within membrane device 81 separates the first pathway 85 from the second pathway 88. Selective membrane 90 functioning to allow a portion of moisture such as in the form of water vapor 91 from the stream of air 83 located within the first pathway 85 to pass therethrough while simultaneously hindering other gases such as oxygen and nitrogen from passing therethrough. The diffusion of water vapor 91 across selective membrane 90 is driven by a difference in chemical potential of water in the two gases. That is, since the oxygen-enriched gas 92 entering at second inlet 87 is extremely dry, there is a driving force for water vapor 91 to pass from the stream of air 83 in the first pathway 85 across the selective membrane 90 to the oxygen-enriched air 92 located in the second pathway 88.

Figure 4:
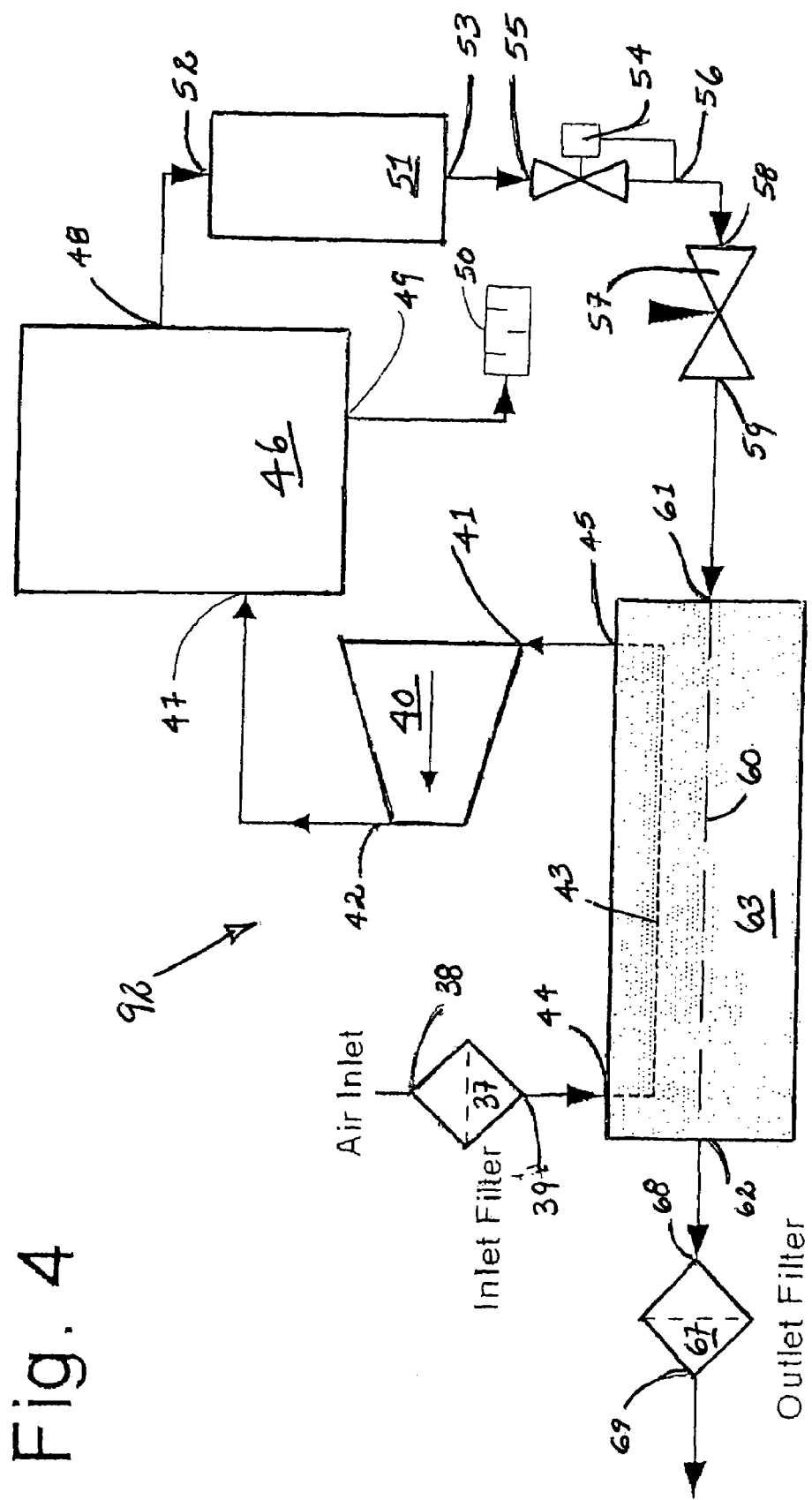
FIG. 4 shows an embodiment of the oxygen concentrator of the present invention.

FIG. 4 shows an embodiment of the oxygen concentrator 92 of the present invention. Oxygen concentrator 92 uses a membrane device 63 similar to the membrane device shown in FIG. 2, but with the first inlet 44 of the membrane device 63 in fluid communication with the outlet 39 of the inlet filter 37 and the first outlet 45 of the membrane device 63 in fluid communication with the inlet 41 of the compressor 40. Thus the same stream of air is passed through the membrane device 63 from the first inlet 44 to the first outlet 45 as shown in FIG. 2, but the stream of air is now at approximately ambient pressure and thus at nominally the same pressure as the oxygen-enriched gas passing from the second inlet 61 to the second outlet 62 of the membrane device 63. This means that the partial pressure of water in the oxygen-enriched gas exiting at the second outlet 62 of the membrane device 63 should be no greater than the partial pressure of water in the air entering the membrane device 63 at the first inlet 44 of the membrane device 63 and thus no greater than the ambient partial pressure of water. As a result, as the oxygen-enriched gas cools on the way to the patient, condensation is inhibited or eliminated. Thus there is no need of a bypass valve as in FIG. 2.

It is sometimes thought by those experienced in the art that a total pressure gradient across the membrane is required to produce flux across the membrane, suggesting that the module would need to be installed as in FIG. 2. However, since flux across the membrane is caused by a partial pressure gradient of a compound in the respective streams, and the oxygen-enriched gas enters the membrane device 63 at the second inlet extremely dry, there is still a partial pressure gradient of water to drive the membrane flux even though the total pressure on the two sides of the membrane is nominally equal.

If membrane device 63 is designed with sufficient membrane area and sufficient membrane permeability for the water vapor, then the partial pressure of water in the oxygen-enriched gas exiting membrane device 63 at the second outlet 62 will be close to the partial pressure of water in the ambient air that the patient is breathing. Thus oxygen-enriched gas will be delivered to the patient with humidity similar to the ambient air without having to make any adjustments for ambient conditions. It is noted that as ambient conditions change, the system will automatically adjust accordingly.

In further regards to the embodiment of FIG. 4, similar to the embodiment of FIG. 2, an added benefit of the embodiment of FIG. 4 is sound abatement which is partially provided by a muffler 50, muffler 50 quieting the oxygen-depleted air as the oxygen-depleted air exits the system. In addition, since the membrane device 63 is connected between the air inlet 37 and the compressor 40, the module dampens some of the sound coming back from the compressor before it exits at the inlet filter 37. This acts to reduce the overall noise of the oxygen concentrator unit 92.

Figure 5:
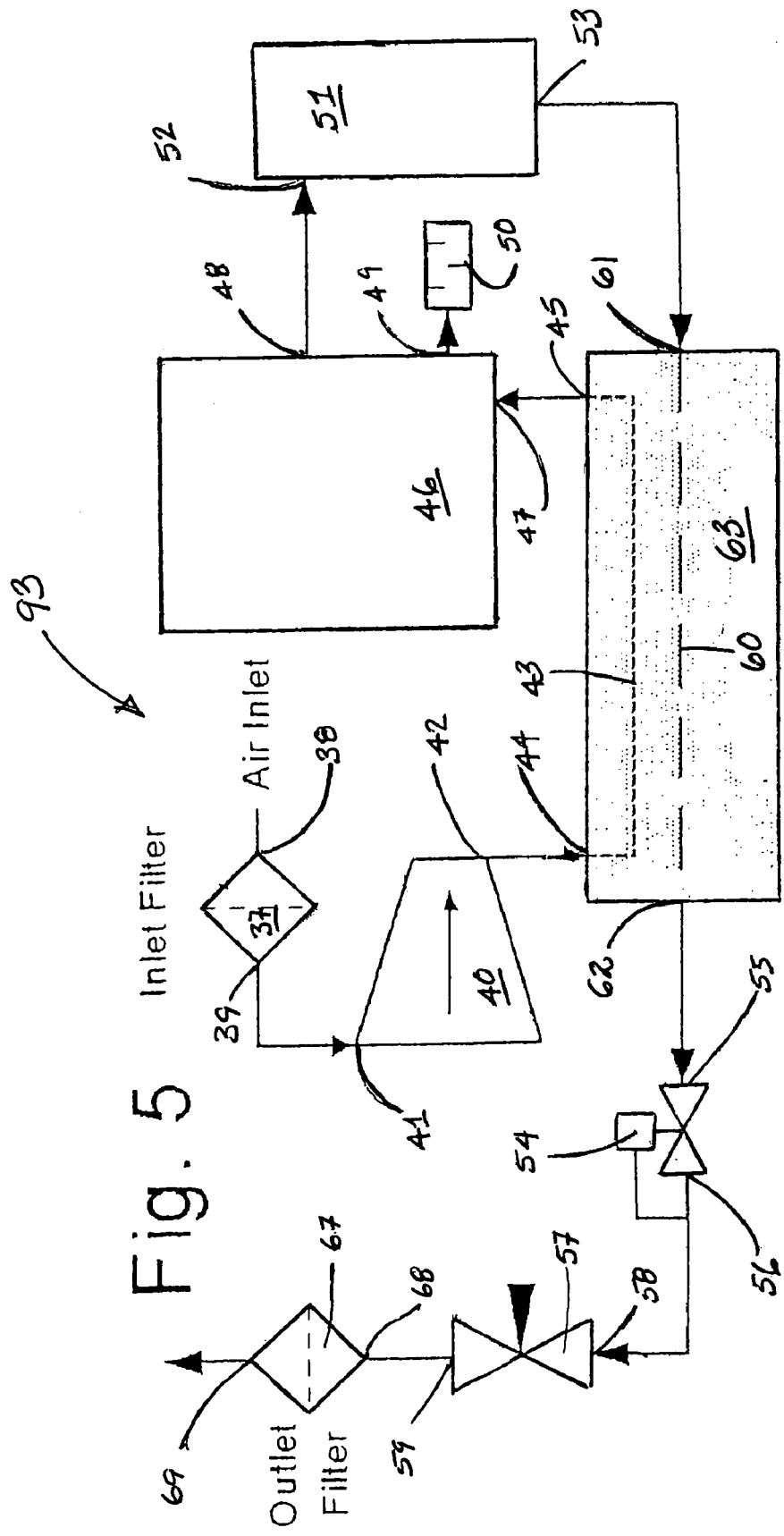
FIG. 5 shows an alternative embodiment of the oxygen concentrator of the present invention.

Referring to FIG. 5, FIG. 5 shows an alternative embodiment 93 of the oxygen concentrator of the present invention. Similar to the oxygen concentrator of FIGS. 2 and 4, the oxygen concentrator of FIG. 5 employs the membrane device 63 for humidification of oxygen-enriched gas. However, unlike the oxygen concentrator of FIGS. 2 and 4, the second inlet 61 of the membrane device 63 is in fluid communication with the outlet 53 of the buffer tank 51, and the second outlet 62 of the membrane device 63 is shown in fluid communication with the inlet 55 of the pressure regulator 54 resulting in the oxygen-enriched gas in membrane device 63 being at a pressure higher than ambient.

However, the pressure of the oxygen-enriched gas in membrane device 63 is lower than the pressure of the air in the first pathway 43 of membrane device 63 by only the pressure drop through the oxygen concentrator adsorption bed 46 and the buffer tank 51, which since the oxygen-enriched gas flow is usually on the order of 5 liters per minute or less, is not a great difference.

As previously noted, the partial pressure of water in the oxygen-enriched gas exiting the membrane device 63 at the second outlet 62 is not higher than the partial pressure of water in the air entering the membrane device 63 at the first inlet 44. The partial pressure of water in the air at the first inlet 44 of the membrane device 63 is also higher than the ambient partial pressure of water by the compression ratio, that is the compressed air pressure divided by the ambient pressure in absolute terms, and may be higher than the vapor pressure of water at ambient temperature, but due to compression is at an elevated temperature and most likely contains no condensate. However, since the vapor pressure of water in the oxygen-enriched gas at the second outlet 62 of the membrane device 63 will be decreased by a similar pressure ratio upon expansion in regulator 54 and valve 57, the partial pressure of water in the oxygen-enriched gas delivered to the patient will be no greater than the ambient partial pressure of water. Thus the system of FIG. 5 also prevents the possibility of condensation in the oxygen-enriched stream.

As noted above, the present invention also includes a method of providing a source of breathable humidified oxygen gas comprising the steps of (1) directing a gas containing oxygen past a first side of a water permeable membrane device 63; (2) separating the oxygen gas from the gas; and (3) directing the oxygen gas past a second side of the water permeable membrane device 63 while maintaining the pressure of the gas on the first side of the water permeable membrane device 63 substantially equal to the pressure of the oxygen gas on the second side of the water permeable membrane device 63 to thereby humidify the oxygen gas to a humidity level substantially equal to or less than a humidity level of the gas on the first side of the water permeable membrane device 63. The aforementioned method can also include the steps of (4) directing a gas containing oxygen past a first side of a water permeable membrane device 63 having a selective membrane 90 with a greater selectivity for water over both nitrogen and oxygen wherein the water permeable membrane device 63 has a selective membrane 90 having a selectivity for water over both nitrogen and oxygen of at least 1, more preferably 10, and most preferably a selectivity for water over both nitrogen and oxygen of at least 100.

The present invention further includes a method of providing a source of breathable humidified oxygen comprising the steps of (1) directing a gas having a first level of humidification past a first side of a water transfer member; (2) directing a breathable amount of oxygen gas having a second level of humidification, with the second level of humidification less than the first level of humidification of the gas, past a second side of the water transfer member while maintaining the pressure of the gas on the first side of the water transfer member substantially equal to the pressure of the oxygen gas on the second side of the water transfer member to thereby humidify the oxygen to a humidity level substantially equal to or less than a humidity level of the gas through water transfer through the water transfer member.

The above method can also include the steps of (3) directing a gas having a first level of humidification past a first side of a membrane device 63 having a selective membrane 90 with a greater selectivity for water over both nitrogen and oxygen; (4) compressing the gas before the gas is directed past the first side of the water transfer member; (5) compressing the gas after the gas has been directed past the first side of the water transfer member; (6) directing the breathable amount of oxygen through a buffer tank to smooth out fluctuations in pressure and flow of the breathable amount of oxygen; (7) using a fan to direct a gas having a first level of humidification past a first side of a water transfer member; (8) directing an oxygen-depleted gas through a muffler to reduce the noise of the oxygen-depleted gas as the oxygen-depleted gas exits the system.

We claim:

1. A method of providing a source of breathable humidified oxygen comprising:
   directing a gas having a first level of humidification past a first side of a water transfer member; and
   directing a breathable oxygen gas having a second level of humidification with the second level of humidification less than the first level of humidification past a second side of the water transfer member while maintaining the pressure of the gas on the first side of the water transfer member substantially equal to the pressure of the oxygen gas on the second side of the water transfer member to humidify the oxygen gas to a humidity level substantially equal to or less than the first level of humidification of the gas trough a transfer of water from the gas to the oxygen gas through the water transfer member.

2. The method of claim 1 wherein the steps of directing a gas having a first level of humidification past a first side of a water transfer member comprises directing a gas having a first level of humidification past a first side of a membrane device having a selective membrane with a greater selectivity for water over both nitrogen and oxygen.

3. The method of claim 1 including the step of compressing the gas before the gas is directed past the first side of the water transfer member.

4. The method of claim 1 including the step of compressing the gas after the gas has been directed past the first side of the water transfer member.

5. The method of claim 1 including the step of directing the breathable amount of oxygen through a buffer tank to smooth out fluctuations in pressure and flow of the breathable amount of oxygen.

6. The method of claim 1 wherein the step of directing a gas having a first level of humidification past a first side of a water transfer member comprises using a fan to direct a gas having a first level of humidification past a first side of a water transfer member.

7. The method of claim 1 including the step of directing an oxygen-depleted gas through a muffler to reduce the noise of the oxygen-depleted gas as the oxygen-depleted gas exits the system.

8. A method of providing a source of breathable humidified oxygen gas comprising:
   directing a gas containing oxygen past a first side of a water permeable membrane;
   separating the oxygen gas from the gas; and
   directing the oxygen gas past a second side of the water permeable membrane while maintaining the pressure of the gas on the first side of the water permeable membrane substantially equal to the pressure of the oxygen gas on the second side of the water permeable membrane to enable water transfer from the gas to the oxygen gas to humidify the oxygen gas to a humidity level substantially equal to or less than a humidity level of the gas on the first side of the water permeable membrane.

9. The method of claim 8 wherein the step of directing a gas containing oxygen past a first side of a water permeable membrane comprises directing a gas containing oxygen past a first side of a water permeable membrane having a selective membrane with a greater selectivity for water over both nitrogen and oxygen.

10. The method of claim 8 wherein the step of directing a gas containing oxygen past a first side of a water permeable membrane comprises directing a gas containing oxygen past a first side of a water permeable membrane having a selective membrane having a selectivity for water over both nitrogen and oxygen of at least 10.

11. The method of claim 8 wherein the step of directing a gas containing oxygen past a first side of a water permeable membrane comprises directing a gas containing oxygen past a first side of a water permeable membrane having a selective membrane having a selectivity for water over both nitrogen and oxygen of at least 100.

12. The method of claim 8 wherein the water permeable membrane comprises a hollow fiber membrane, a flat sheet membrane, or a spiral wound membrane.

13. A method of providing a source of breathable humidified oxygen gas comprising:
   directing a gas having a first level of humidification past a first side of a water permeable membrane; and
   directing a breathable oxygen gas having a second level of humidification with the second level of humidification less than the first level of humidification of the gas past a second side of the water permeable membrane while maintaining the pressure of the gas on one side of the water permeable membrane substantially equal to the pressure of oxygen gas on the second side of the water permeable membrane to transfer water from the gas on the first side of the water permeable membrane to the oxygen gas on the second side of the water permeable membrane to humidify the oxygen gas to a humidity level substantially equal to or less than a humidity level of the gas.

* * * * *